United States Patent [19]

Criddle

[11] 4,205,668
[45] Jun. 3, 1980

[54] ELLIPTICAL DIFFUSER DRAPE

[75] Inventor: Ernest E. Criddle, Ottawa, Canada

[73] Assignee: Minister of National Defence of Her Majesty's Canadian Government, Ontario, Canada

[21] Appl. No.: 934,802

[22] Filed: Aug. 18, 1978

[30] Foreign Application Priority Data

May 24, 1978 [CA] Canada .................................. 303960

[51] Int. Cl.² ............................................. A61B 19/06
[52] U.S. Cl. ............................. 128/132 D; 128/207.26
[58] Field of Search .............. 128/132 D, 132 R, 1 R, 128/68.1, 82.1, 184

[56] References Cited

U.S. PATENT DOCUMENTS

| 3,881,477 | 5/1975 | Von Otto | 128/132 D |
| 3,927,667 | 12/1975 | Criddle | 128/132 D |

FOREIGN PATENT DOCUMENTS

| 2357686 | 5/1975 | Fed. Rep. of Germany | 128/132 D |
| 2522667 | 1/1976 | Fed. Rep. of Germany | 128/132 D |

*Primary Examiner*—Lawrence W. Trapp
*Attorney, Agent, or Firm*—Larson, Taylor and Hinds

[57] ABSTRACT

A diffuser drape for use in surgical procedures includes a sheet with an elliptical aperture therein for placing over the patient with the aperture defining the area of the proposed surgical incision; an annular, elliptical air duct on and attached to the sheet surrounding the aperture, the air duct including a diffuser ring on its lower, inner side surrounding the aperture when in use for diffusing clean air radially outwardly into the area above the aperture to keep the area of the incision clean, the ring having a non-uniform elliptical configuration, i.e. the ends of the diffuser ring are narrower than the sides thereof; and an air inlet integral with the air duct at each end thereof for introducing clean air into the duct for passage through the diffuser ring and the remainder of the duct.

5 Claims, 3 Drawing Figures

ELLIPTICAL DIFFUSER DRAPE

This invention relates to a diffuser drape for use in surgical operations.

Briefly, in the prior art, Marsh and Beck [R. C. Marsh and W. C. Beck, "Target Zone Protection from Air Contamination by a New Airflow Modality—Vortex Airflow", Guthrie Clin. Bull. 38, 52 (1968)] noted the effectiveness of a clean room during surgical operations and the simplicity of a clean bench for accomplishing many clean room processes. They attempted to protect a surgical wound site with clean air flowing inwardly from a diffuser surrounding the site. The area of the diffuser had to equal the area protected, and the diffuser required a lip at its upper edge to reduce tubulence and entrainment of room air into the working area. It was also necessary to use an air flow of 120 fpm (feet per minute) to provide protection, the resulting clean air rising upwardly in a cylindrical pattern from the diffuser well.

The present inventor, E. E. Criddle, in Canadian Pat. No. 919,978, issued Jan. 30, 1973 and in U.S. Pat. No. 3,719,136, issued Mar. 6, 1973, proposed the use of a barrier of air flowing inwardly like that of Marsh and Beck, and outwardly as well. A practical diffuser drape for providing a clean air zone is disclosed in the E. E. Criddle et al U.S. Pat. No. 3,927,667, issued Dec. 23, 1975. Air from the diffuser of the last-mentioned patent forms a tulip-shaped curtain, and provides clear air flowing upwardly at 180 fpm from the wound site. A diffuser is built into the surgical drape with an elliptical configuration, and a pair of air supply ducts are provided under the drape for use in practical surgery.

The R. E. Von Otto U.S. Pat. No. 3,692,024, issued Sept. 19, 1972 discloses a surgical appliance of elliptical or circular shape, including rows of jets for protecting a surgical site and the surgeon's hands. The jets are designed to merge, forming a continuous conical curtain. However, it is likely that the jets would entrain and merge with room air, becoming contaminated two jet diameters downstream [see D. S. Miller and K. J. Zanker, "The Use of Air Jets to Produce a Local Clean Area in a Contaminated Atmosphere", The British Hydromechanics Research Association, Cranfield, England (Sept. 1967)]. Von Otto's U.S. Pat. No. 3,881,477, issued May 6, 1975 discloses a rectangular surgical appliance containing several rows of jets or ports for avoiding entrainment of external air. Obviously, the device can have any closed configuration. Like Marsh and Beck, Von Otto relies on jets, but fails to mention that jet flows cannot be trusted to retain their integrity.

In all of the above-mentioned cases, the distance from the wound site to normal room air is short—a few inches to one foot. In order to protect the wound, air flows of 100 to 250 fpm are required. The high flow rates guard against turbulent inflow, and sweep away air carried inwardly by movement of the surgeon's hands. Such an upward air velocity will entrain air at its periphery, and the entrained air is often from the area of the surgeon's hips. This area is the most likely source of undesirable colony-forming bacteria. Drawn closer to the operating zone, the bacteria may settle on the surgeon's gloves or instruments, or on the sterile drape and then be carried manually to the wound site.

Many surgeons have expressed concern about wound drying. Room air turbulence and wound thermals (heat from the wound site) create draughts of approximately 50 fpm which are tolerable. Jets of 100 to 150 fpm have been observed to produce drying rates and wound flesh cooling of double to triple the normal rates. Higher jet velocities may well have still worse effects.

While the elliptical diffusers disclosed by the present inventor's U.S. Pat. No. 3,927,667 mentioned above provide relatively good protection of a small surgical wound site, it has been found that the barrier of clean air breaks down when the area of protection is increased to include larger areas for example in transthoracic procedures and knee arthroplasty. Moreover, the use of flexible air ducts under the surgical drape may prove troublesome. Even in the laboratory, the flexible ducts for supplying clean air are difficult to manage, the duct in the drape tending to kink where the flexible duct enters the drape causing reduced flow rates. Such a reduction in air flow rate could easily go unnoticed in a busy operating room.

The object of the present invention is to provide a new diffuser drape for use in surgical operations which overcomes the above-mentioned problems, providing relatively good protection of a wound site.

Accordingly, the invention relates to an elliptical diffuser drape comprising a sheet member with an elliptical aperture therein; an inflatable, porous, elliptical air duct mounted on said sheet member and surrounding said aperture above the sheet member when in use; a diffuser ring on the lower side of said air duct surrounding said aperture for diffusing clean air radially outwardly into the area above said aperture, said ring having a non-uniform elliptical configuration; and an air inlet at each end of said air duct for introducing clean air into said air duct for passage through said diffuser ring and through said porous air duct.

By non-uniform elliptical is meant a planar elliptical ring the outer edge of which is defined by a first ellipse, and the inner edge of which is defined by a second ellipse having a major axis such that foci of the first and second ellipses are relatively close together, with the foci of the second ellipse outside the foci of the first ellipse. Normally, with uniform concentric ellipses, the ring would be elliptical and of constant width. With the present non-uniform elliptical ring, the ends are narrow and the ring is widest at the longitudinal centre of each side.

It should be noted that clean air can flow outwardly through any point in the air duct, the rate of air flow being determined by the type of material being used. The usual material is cotton or a blend of cotton and a synthetic material such as Fortrel (a registered trade mark for a polyester type synthetic fibre). Clean air flows outwardly from the perimeter of the air duct to remove contaminants emanating from the surgeon's body or from other points in the operating room, upwardly from the top of the air duct, inwardly through the diffuser ring and downwardly through the base of the air duct and the underlying sheet member. It has been found advantageous to use more open types of material for the perimeter and top of the air duct than for the lower nonuniform annular diffuser ring so that air flow velocities over the wound are kept to a minimum.

The invention will now be described in greater detail with reference to the accompanying drawings, which illustrate a preferred embodiment of the invention, and wherein.

With reference to the drawings, the diffuser drape of the present invention includes a sheet 1, which is merely a small surgical drape which, in use, is placed on top of standard modern surgical drapes. The sheet 1 is provided with an elliptical aperture 2, and the sheet is placed over the patient in such a manner that the opening 2 surrounds the proposed surgical incision.

Figure 1:
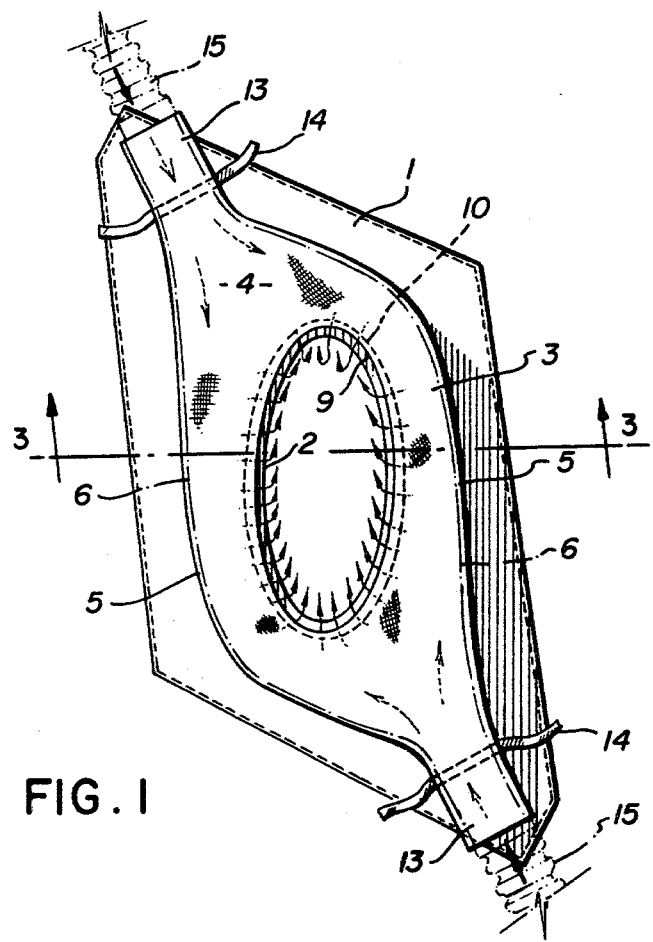
FIG. 1 is a schematic plan view of a diffuser drape in accordance with the present invention in an inflated condition.
Figure 2:
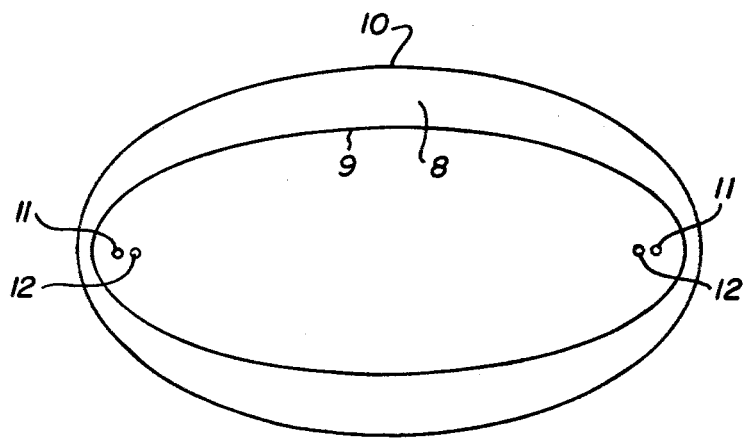
FIG. 2 is a schematic plan view of a diffuser ring portion of the apparatus of FIG. 1.

A generally elliptical air diffuser duct 3 is provided on the sheet 1 surrounding and concentric with aperture 2. The sheet 1 is generally in the shape of a parallelogram, and is large enough to form a small border around the air duct 3. The air duct 3 includes a top portion 4 connected to outer sides or gussets 5 by lines of stitching 6, a base 7 (FIG. 3) and a lower ring 8 which forms an interior side wall or diffuser ring when the duct is inflated. As best illustrated in FIG. 2, inner and outer edges 9 and 10 of the diffuser ring 8 define ellipses. The foci 11 of the inner ellipse are located outside of the foci 12 of the outer ellipse, whereby the shape defined is a nonuniform elliptical ring and both foci are located within the inner ellipse. The base 7 and diffuser ring 8 when stitched together, have approximately the same shape and overall dimensions as the top portion 4.

Inlet tubes 13 integral with the air duct 3 enter the latter above the sheet 1 at each end of the duct 3 at an angle of between 22° and 35° to the longitudinal axes of the ellipses defined by the aperture 2 and the inner edge 9 of the diffuser ring 8. Tapes 14 are provided for attaching air supply hoses 15 to the inlet tubes 13. The hoses 15 are inserted into the tubes 13 above the sheet 1 and the tapes are wrapped around the tubes 13.

The sheet 1, air duct 3, top portion 4, gussets 5, base 7, diffuser ring 8 and inlet tubes 13 are all formed of cotton or cotton/synthetic blends such as cotton and Fortrel. Suitable fabrics include 140 count Wabasso Everware (registered trade mark) and 5 oz Dominion Premiere Poplin (trade name), which is a mixture of 65% Fortrel and 35% cotton and which offers greater resistance to air flow than Everware.

By way of example, the difuser drape may be formed of Wabasso Everware and may have a 16″ by 8″ opening for surgical procedures with a top annulus 4″ across and extended to form the top of the inlet tubes 13. The non-uniform elliptical lower diffuser ring may be formed of Premiere Poplin and measure 2.25″ across at its sides and 1″ across at the ends of the oval. The distance from the annulus to the centre along the short axis is 4″ (1.8 times greater than the 2.25″ annular width at that line), and from the annulus to a point midway between the foci 11 and 12 at each end of the diffuser ring is 1.4″ (1.4 times the annular width of 1″ at that line).

Figure 3:
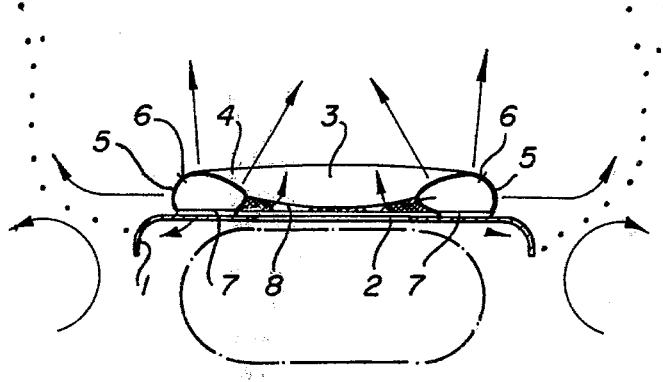
FIG. 3 is a cross-sectional view of the drape of FIG. 1 in use, taken generally along line 3—3 of FIG. 1.

The construction of the elliptical diffuser drape is relatively simple. All pieces are cut with the longitudinal axes of ellipses oriented similarly on the warp of the cloth. One quarter inch seam allowances are left, and markers are placed on the longitudinal axes at the seams. The top portion 4 is stitched to the diffuser ring 8 at their inner edge 9. The diffuser ring 8 is sewn at its outer edge to the inner edge of the base 7, both of which are sewn to the sheet 1 at the same locations. The air duct may then be closed by one of two method. The first method is to sew the sides or gussets 5 to the top portion 4 at lines of stitching 6 and to the base 7; the seam between the sides 5 and the base 7 may then be sewn to the base over most of its length, leaving the inlet tubes 13 free of the sheet 1 so that tapes 14 can secure air supply hoses 15 inside the inlet tubes 13. It should be noted that FIG. 3 is slightly inaccurate in this respect, because the base 7 of the air duct 3 is shown above the sheet 1. In fact, the base 7 normally bears against the sheet 1. Alternatively, in a second method, the sides 5 may be sewn to the base 7 and at least partly sewn to the sheet 1 leaving the inlet tubes 13 free as in the first method; then the air duct is closed by joining the sides 5 to the top portion 4 at lines of stitching 6.

In use, the air flow pattern achieved with the diffuser drape is that illustrated by the arrows in FIG. 3. Air will flow outwardly from the outer perimeter and upwardly from the top portion of the air duct 3 to reject airborne contaminants emanating from the surgeon's body or otherwise found in the atmosphere of an operating room. Because the perimeter of the zone of protection extends reasonably far outwardly, low air velocities provide protection against draughts and air carried along during movement of the surgeon's hands. Air will flow inwardly from the lower ring and then upwardly as shown. Some air is expected to diffuse, albeit slowly, through the double thickness of the base 7 and the sheet 1 to ventilate the zone around the patient's body. This should prevent the buildup of airborne contaminants under the drape next to the patient and so reduce the concentration of contaminants which waft to the wound site when the drape is moved or pumped like a bellows during surgical procedures.

With a uniform lower elliptical diffuser ring, air flows tangentially inwardly from the inner circumference of the ring and focuses on the foci of such inner circumference and the line between such foci. Air from the outer circumference of the ring will flow inwardly to focus on the foci of such outer circumference and the line between them. Air from the annulus between the inner and outer circumferences will focus on zones between such limits, and will provide jets of air from the zones close to the pairs of foci of the inner and outer circumferences; these jets are very noticeable when one of the foci is located within the annulus.

With the non-uniform elliptical diffuser ring 8 of the present invention, air flows from the inner circumference of the ring tangentially inwardly toward the line joining foci 11 of the inner circumference and inwardly at a tangent to the outer circumference towards the foci 12 and the line joining the foci 12. If the width of the diffuser ring along its short axis is one-half the distance from the ring to the centre, then air from the sides of the ring must cover the larger corresponding area within the inner circumference, i.e. the velocity of air through the fabric of the diffuser ring 8 will decrease as this air fills the larger area bounded by the ring. Likewise, if the width of the diffuser ring along its long axis is one-half the distance from the ring annulus to the zone of the two foci 11 and 12 and if all foci 11 and 12 are located within the inner ring, then air from the ends of the ring must cover the larger corresponding area within the ring.

In practice, the diffuser ring 8 will be partially blocked by the presence of a seam at the inner edge 9 and very slightly blocked by bearing against sheet 1. In the example of a practical diffuser drape given above, when the 2.25″ sides and 1″ ends of the annulus of the lower ring are reduced by a quarter inch seam effectively to 2" and 0.75", air from these sections of the annulus must cover distances of 4" to the center and 1.4" to the zones of the foci, respectively. The effective ratios of these diffusers to the central areas are then all approximately one half.

There has thus been described a diffuser drape, which avoids entraining air plumes or jets because of its configuration and geometric arrangement. The diffuser provides a barrier of clean air between the surgeon and the surgical site.

The embodiments of the invention in which an exclusive property or privilege is claimed are defined as follows:

1. An elliptical diffuser drape for use in surgical procedures comprising a sheet member with an elliptical aperture therein; an inflatable, porous, elliptical air duct mounted on said sheet member and surrounding said aperture above said sheet member when in use; a diffuser ring on the lower side of said air duct surrounding said aperture for diffusing clean air radially outwardly into the area above said aperture, said ring having a non-uniform elliptical configuration wherein the inner and outer edges of said ring are defined by ellipses with the foci of the inner and outer ellipses close together and the foci of the inner ellipse outside of the foci of the outer ellipse such that the longitudinal ends of said ring are narrower that the longitudinal sides; and an air inlet at each end of said air duct for introducing clean air into said air duct for passage through said diffuser ring and through said porous air duct.

2. A diffuser drape according to claim 1, wherein said air duct is formed of a material which permits the passage of clean air radially outwardly through any point in the air duct as well as through the diffuser ring.

3. A diffuser drape according to claim 2 wherein clean air is passed through said air duct more easily than through said diffuser ring.

4. A diffuser drape according to claim 1, wherein each said air inlet is integral with said air duct and is mounted on said sheet member with the air duct for connection to a source of clean air.

5. A diffuser drape according to claim 1, 2 or 3, wherein said sheet is generally in the shape of a parallelogram extending a short distance beyond the periphery of the air duct and air inlets.

* * * * *